(12) United States Patent
Steinmetz et al.

(10) Patent No.: US 6,602,489 B2
(45) Date of Patent: Aug. 5, 2003

(54) COMPACT HAIRSPRAY PRODUCT CONSISTING OF HAIRSPRAY CONCENTRATE, CONTAINER AND FINE SPRAY PUMP WITH PRE-PRESSURIZATION

(75) Inventors: Uwe Steinmetz, Reinheim (DE); Thomas Starke, Muehltal (DE); Franz Steigerwald, Griesheim (DE)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 09/937,893

(22) PCT Filed: Jan. 30, 2001

(86) PCT No.: PCT/EP01/00958
§ 371 (c)(1),
(2), (4) Date: Feb. 21, 2002

(87) PCT Pub. No.: WO01/56536
PCT Pub. Date: Aug. 9, 2001

(65) Prior Publication Data
US 2002/0150542 A1 Oct. 17, 2002

(30) Foreign Application Priority Data
Feb. 3, 2000 (DE) .......................................... 100 04 769

(51) Int. Cl.⁷ ........................... A61K 7/00; A61K 7/06; A61K 31/74
(52) U.S. Cl. .................. 424/47; 424/70.11; 424/78.02; 424/DIG. 1; 424/DIG. 2; 514/957
(58) Field of Search ................ 424/47, 78.02, 424/70.11, DIG. 1, DIG. 2; 514/957

(56) References Cited

U.S. PATENT DOCUMENTS

| 5,032,387 A | 7/1991 | Hill et al. |
| 5,626,835 A | 5/1997 | Malawer et al. |

FOREIGN PATENT DOCUMENTS

| DE | 39 41 572 A | 6/1991 |
| EP | 0 460 123 B1 | 6/1993 |

OTHER PUBLICATIONS

Schrader: "Grundlagen Uns Rezepturen Der Kosmetika", 2. AUFLAGE 1989, pp. 770–773.

*Primary Examiner*—Shelley A. Dodson
(74) *Attorney, Agent, or Firm*—Michael J. Striker

(57) ABSTRACT

The compact hair spray product includes a pressure-tight and diffusion-proof container containing a hair spray concentrate and equipped with a fine-spray pump with a cylindrical region made of a material that resists swelling by organic solvents. The fine spray pump has a maximum pump lift of 0.12 mL and pilot pressure buildup. The hair spray concentrate has a viscosity that confers good sprayability and contains at least one hair-strengthening polymer, an alcoholic solvent for the hair-strengthening polymer, at least one organic solvent additive capable of reducing the viscosity of the concentrate and increasing the vapor pressure of the concentrate and optionally a drying-retarding solvent additive.

14 Claims, No Drawings

COMPACT HAIRSPRAY PRODUCT CONSISTING OF HAIRSPRAY CONCENTRATE, CONTAINER AND FINE SPRAY PUMP WITH PRE-PRESSURIZATION

BACKGROUND OF THE INVENTION

The object of the invention is a compact hair spray product comprising a hair spray concentrate, a pressure-tight and diffusion-proof container and a fine-spray pump with pilot pressure buildup.

Hair spray products are usually sold either as aerosol sprays packed in aerosol containers and containing propellants or as propellant-free pump sprays which are sprayed by means of a mechanical spray pump, the pump lift volume usually being 120–190 μL. Because of their better performance and better application properties, aerosol sprays are substantially more important. The conventional aerosol hair sprays, however, have the drawback that such products require relatively large and unwieldy containers. This, in turn, leads to unattractive and difficult-to-configure packaging forms. Commonly used, for example, are 250-mL cans made of tinplate or aluminum in conventional cylindrical shape. The relatively large size is due to the comparatively large gas space which is devoid of active substances and which is needed for the propellant. Although pump sprays use no propellant and, hence, can be sold in less voluminous packages compared to aerosol cans, one has to put up with a definite loss in application properties. Consumers feel that, compared to aerosol sprays, the common, known pump sprays are for the most part wetter and coarser and that they have a longer drying time and a coarser drop spectrum. Their market share is correspondingly small. Moreover, because of the relatively low attainable concentration of the hair-strengthening polymer in aerosol sprays and the need for a large headspace, it has thus far not been possible to produce compact aerosol hair spray products which in terms of both application properties and economy in use match the aerosol sprays in the usual 250-mL package sizes.

Hair sprays are usually used in the form of polymer solutions in an alcoholic medium. The polymer concentration is relatively limited. According to Schrader, "Grundlagen und Rezepturen der Kosmetika" [Fundamentals and Formulations of Cosmetics], 2nd edition, 1989, page 772, the typical polymer content of a hair spray is 2–4%. Higher polymer contents lead to many problems which are due primarily to a marked increase in viscosity of the composition. For example, when the polymer concentration is increased, the droplet size of the sprayed composition based on the usual alcoholic solvent increases unacceptably to more than 100 μm. Good pump hair sprays have an average droplet size of about 80 μm, the smaller the better (for example 50 μm). The drawbacks of excessively large drops are the wetness effect, the pearl chain effect involving the formation of pearl-like droplets which on the hair are visible, poorly flowing and poorly drying, moreover long drying times, poor distribution on the hair, deterioration of the spray pattern etc. Besides the average droplet size, the droplet size distribution is determining for the quality of a hair spray, because even a relatively small number of very large drops brings about major drawbacks. The dv(50) and dv(90) values provide a measure of the droplet size distribution. These values give the maximum diameter of 50% or 90% of all droplets. For typical aerosol hair sprays, the average dv(50) value is about 40 μm and the average dv(90) value about 75 μm. For typical pump hair sprays, the average dv(50) value is about 75 μm and the average dv(90) value about 120 μm. The dv(90) value, in particular, should not exceed 140 μm and preferably not 130 μm. The sprays will otherwise be perceived as being very wet.

European Patent EP 0 460 123 A discloses a one-phase solvent mixture of $C_2$–$C_4$ alcohols, water and a lower alkane, selected from among n-pentane, n-hexane and iso-hexane. This solvent mixture can be used in non-aerosol hair sprays. Hair spray concentrates and compact hair sprays are not described.

Desirable therefore are small, compact hair spray products which compared to the usual aerosol sprays and the usual pump hair sprays present a comparable economy of use at a fraction of the container volume, while at the same time presenting application properties, for example a strengthening efficacy and spray performance, that do not have the drawbacks of common pump hair sprays, but approximate those of aerosol sprays and, from the standpoint of environmental protection, also present a desirable, improved volatile organic compound [VOC] balance.

SUMMARY OF THE INVENTION

We have now found that this objective can be reached by use of a compact hair spray product comprising a special hair spray concentrate, a pressure-tight and diffusion-proof container and a special fine-spray pump with pilot pressure buildup.

The object of the invention therefore is a compact hair spray product comprising
- (A) a hair spray concentrate having a viscosity permitting good sprayability and containing
  - (a1) at least one hair-strengthening polymer,
  - (a2) an alcoholic solvent for polymer (a1),
  - (a3) at least one organic solvent additive capable of reducing the viscosity of the concentrate and increasing the vapor pressure of the concentrate, and
- (B) a pressure-tight and, for concentrate (A), diffusion-proof container and
- (C) a fine-spray pump with
  - (c1) a cylindrical region made of a material that resists swelling by the organic solvent additive (a3),
  - (c2) a maximum lift of 0.12 mL and
  - (c3) pilot pressure buildup.

The hair spray concentrate preferably also contains a drying-retarding solvent additive (a4).

The object of the present invention is eminently suited for the production of hair spray products of compact design, for example with a volume of 40 to 60 mL, presenting an economy of use approximating that of typical 250–300 mL aerosol hair spray cans.

For purposes of the invention, by compact hair spray product is meant a hair spray product of more compact design than that of a typical aerosol hair spray, namely a product with a filling volume of less than 250 mL and particularly of at the most 150 mL. Preferred are filling volumes from 10 to 100 mL, particularly from 20 to 80 mL and especially from 40 to 60 mL. For purposes of the invention, by hair spray concentrate is meant a composition comprising at least one hair-strengthening polymer at a concentration that is higher than that of common hair sprays which typically is 4 wt. % and for hair lacquers 6 wt. %. The polymer concentration is preferably higher than 8% wt. % and particularly higher than 10 wt. %, based on the total composition. The maximum polymer concentration is preferably 20 wt. %.

For purposes of the invention, by viscosity permitting good sprayability is meant a viscosity at which the average droplet size obtained with a Seaquist-Perfect PZ1/100 HVT fine-spray pump is less than 100 μm and preferably less than 80 μm or for which the dv(90) value is at the most 140 μm and preferably at the most 130 μm. The average droplet size and droplet size distribution can be determined, for example, with the aid of a particle-sizing instrument based on laser radiation diffraction, for example a Malvern Particle Sizer instrument. The preferred kinematic viscosity is at the most 10 mm$^2$.s, and preferably at the most 5 mm$^2$.s, determined with a RheoStress 100 rotational viscometer, supplied by Haake, at a temperature of 25° C. and a shear gradient from 0.5 to 1400 s$^{-1}$.

Suitable hair-strengthening polymers are selected from the group consisting of synthetic or natural or modified natural polymers, which in each case can have a nonionic, cationic, anionic or amphoteric character. A mixture of several of these polymers can also be used. According to the invention, by hair-strengthening polymer is meant a polymer which when used in the form of a 0.01 to 5% aqueous, alcoholic or aqueous-alcoholic solution is capable of depositing a polymer film on the hair thus strengthening the hair.

Suitable synthetic, nonionic, film-forming, hair-strengthening polymers are, for example, the homopolymers of vinylpyrrolidone, vinylcaprolactam or N-vinylformamide. Other suitable synthetic film-forming, nonionic, hair-strengthening polymers are, for example, the copolymers of vinylpyrrolidone and vinyl acetate, the terpolymers of vinylpyrrolidone, vinyl acetate and vinyl propionate, polyacrylamide sold, for example, by CHEM-Y, Emmerich, under the tradename Akyponine® P 191 and by Seppic under the tradename Sepigel® 305; polyvinyl alcohols sold, for example, by Du Pont under the tradename Elvanol® or by Air Products under the tradename Vinol® 523/540; and polyethylene glycol/polypropylene glycol copolymers sold, for example, by Union Carbide under the tradename Ucon®.

Suitable natural or modified natural, film-forming polymers with hair-strengthening action are, for example, the chitosans with a molecular weight from 20,000 to about 5 million g/mol. Moreover, various saccharide types can be used, such as polysaccharides or mixtures of oligo-, mono- and disaccharides, sold, for example, by Cerestar, Brussels, under the tradename C-PUR®. Other suitable natural polymers are Chinese balsamic resin, guar or guar derivatives and cellulose derivatives, for example hydroxypropylcellulose, with a molecular weight from 30,000 to 50,000 g/mol, sold, for example, by Lehmann & Voss, Hamburg, under the tradename Nisso S1®. Another natural polymer is shellac which can be used in neutralized, partly neutralized or non-neutralized form.

Suitable anionic polymers contain acid groups that can be neutralized with appropriate bases. The acid groups are preferably selected from among —COOH,—SO$_3$H,— OSO$_3$H,—OPO$_2$H and —OPO$_3$H$_2$. Carboxylic acid groups are particularly preferred. From 50 to 100% of the acid groups are preferably in anionic or neutralized form. The neutralizing agent can be any organic or inorganic base suitable for cosmetic purposes. Examples of bases are aminoalcohols, for example aminomethylpropanol (AMP), triethanolamine or monoethanolamine, and ammonia, NaOH etc.

The hair-strengthening anionic polymer can be a natural or synthetic homopolymer or copolymer with acid groups-containing monomer units optionally copolymerized with comonomers devoid of acid groups. Suitable monomers are unsaturated compounds capable of undergoing free radical-initiated polymerization and which bear at least one acid group, particularly carboxyvinyl monomers. Suitable acid groups-containing monomers are, for example, acrylic acid, methacrylic acid, crotonic acid, itaconic acid, maleic acid or maleic anhydride or a monoester thereof, fumaric acid or a monoester thereof, aldehydocarboxylic acids or ketocarboxylic acids. Other suitable anionic polymers are the anionic polyurethanes.

Comonomers not bearing acid groups as substituents are, for example, acrylamide, methacrylamide, alkyl and dialkylacrylamide, alkyl and dialkylmethacrylamide, alkyl acrylate, alkyl methacrylate, vinylcaprolactone, vinylpyrrolidone, vinyl esters, vinyl alcohol, propylene glycol or ethylene glycol, amino-substituted vinyl monomers, for example dialkylaminoalkyl acrylate, dialkylaminoalkyl methacrylate, monoalkylaminoalkyl acrylate and monoalkylaminoalkyl methacrylate, the alkyl groups of these monomers preferably being $C_1$–$C_7$-alkyl groups and particularly $C_1$–$C_3$-alkyl groups.

Suitable anionic polymers are, in particular, the following compounds, non-crosslinked or crosslinked with polyfunctional agents: homopolymers of acrylic acid or methacrylic acid, copolymers of acrylic acid or methacrylic acid and monomers selected from among acrylate or methacrylate esters, acrylamides, methacrylamides and vinylpyrrolidone, homopolymers of crotonic acid and copolymers of crotonic acid and monomers selected from among vinyl esters, acrylate or methacrylate esters, acrylamides, methacrylamides and copolymers with polyethylene oxide. A suitable natural polymer is, for example, shellac.

Preferred anionic polymers are crosslinked or non-crosslinked vinyl acetate/crotonic acid copolymers (INCI[1] name: VA/crotonates copolymer) and vinyl acetate/crotonic acid/polyethylene oxide copolymers. Also preferred are the partially esterified copolymers of vinyl methyl ether and maleic anhydride, for example methyl vinyl ether/ monoethyl maleate ester or monobutyl maleate ester copolymer (INCI name: ethyl ester of PVM/MA copolymer, butyl ester of PVM/MA copolymer). Other suitable anionic polymers are, for example, the copolymers of acrylic acid, alkyl acrylates and N-alkylacrylamide (INCI name: acrylates/ acrylamide copolymer), particularly acrylic acid/ethyl acrylate/N-tert.butylacrylamide terpolymers, and copolymers of one or more $C_1$–$C_5$-alkyl acrylates, particularly $C_2$–$C_4$-alkyl acrylates and acrylic acid or methacrylic acid (INCI name: acrylates copolymer), particularly methacrylic acid/ethyl acrylate/butyl acrylate terpolymers. Also suitable are the terpolymers of vinyl acetate, crotonate and vinyl alkanoate, particularly vinyl acetate/crotonate/vinyl neodecanoate copolymers or vinyl acetate/crotonate/vinyl propionate copolymers (INCI names: VA/crotonates/vinyl neodecanoate copolymer and VA/crotonates/vinyl propionate copolymer).

[1] INCI=International Nomenclature of Cosmetic Ingredients—Translator

Suitable amphoteric polymers are those which besides acid or anionic groups contain as additional functional groups basic or cationic groups, particularly primary, secondary, tertiary or quaternary amino groups. Examples of these are the copolymers derived from an alkylacrylamide (particularly octylacrylamide), an alkylaminoalkyl methacrylate (particularly tert.butylaminoalkyl methacrylate) and two or more monomers consisting of acrylic acid, methacrylic acid or an ester thereof (INCI name: octylacrylamide/acrylates/butylaminoethyl methacrylate copolymer) supplied, for example, by NATIONAL STARCH, USA, under the tradename Amphomer® or Amphomer® LV-71. Other suitable amphoteric polymers are the copolymers derived from at least one monomer of the first kind containing quaternary amino groups and at least one monomer of the second kind containing acid groups. Examples of such copolymers are the copolymers of acrylic acid, methyl acrylate and methacrylamidopropyltrimethylammonium chloride (INCI: name: polyquaternium 47), such as those sold by Calgon under the tradename Merquat® 2001, copolymers of acrylamidopropyltrimethylammonium chloride and acrylates, for example those sold by Stockhausen under the commercial name W 37194, or the copolymers of acrylamide, acrylamidopropyltrimethylammonium chloride, 2-amidopropylacrylamide sulfonate and dimethylaminopropylamine (INCI name: polyquaternium 43), sold for example, by Societe Francaise Hoechst under the tradename Bozequat® 4000. Also suitable are the polymers bearing betaine groups, for example the copolymers of methacryloylethylbetaine and two or more monomers derived from acrylic acid or a simple ester thereof, known under the INCI name of methacryloyl ethyl betaines/acrylates copolymer.

Suitable polymers with basic groups preferably have a molecular weight of at least 50,000 g/mol and particularly from 100,000 to 6,000,000 g/mol and they have nitrogen-containing groups, for example primary, secondary or tertiary amino groups. The basic polymers can be partly or completely neutralized with a suitable cosmetically compatible acid and thus be in the cationic form. Suitable acids are, for example, formic acid, pyrrolidonecarboxylic acid, lactic acid etc. The basic group is either contained in the polymer chain or, preferably, is a substituent of one or several monomers. The polymer with basic groups can be a natural or synthetic homopolymer or copolymer with amine-substituted monomer units and optionally nonbasic comonomers. Suitable polymers with basic groups are, for example, the copolymers of amine-substituted vinyl monomers and non-amine-substituted monomers. Amine-substituted vinyl monomers are, for example, dialkylaminoalkyl acrylate, dialkylaminoalkyl methacrylate, monoalkylaminoalkyl acrylate and monoalkylaminoalkyl methacrylate, the alkyl groups of these monomers preferably being lower alkyl groups such as, for example, $C_1$–$C_7$-alkyl groups and particularly $C_1$–$C_3$-alkyl groups.

Non-amine-substituted comonomers are, for example, acrylamide, methacrylamide, alkyl and dialkyl acrylamide, alkyl and dialkyl methacrylamide, alkyl acrylate, alkyl methacrylate, vinylcaprolactone, vinylpyrrolidone, vinyl esters, vinyl alcohol, maleic anhydride, propylene glycol or ethylene glycol, the alkyl groups of these monomers preferably being $C_1$–$C_7$-alkyl groups and particularly $C_1$–$C_3$-alkyl groups.

Suitable polymers with cationic groups preferably contain quaternary amino groups. The cationic polymers can be homopolymers or copolymers, wherein the quaternary nitrogen groups are contained either in the polymer chain or preferably as a substituent of one or more monomers. The ammonium groups-containing monomers can be copolymerized with the above-said non-amine-substituted monomers. Suitable ammonium-substituted vinyl monomers are, for example, trialkylmethacryloxyalkylammonium, trialkylacryloxyalkylammonium, dialkyldiallylammonium and quaternary vinylammonium monomers with cyclic, cationic nitrogen-containing groups, such as pyridinium or imidazolium, or quaternary pyrrolidones, for example alkylvinylimidazolium, alkylvinylpyridinium, or alkylvinylpyrrolidone salts. The alkyl groups of these monomers are preferably lower alkyl groups, for example $C_1$–$C_7$-alkyl groups, and particularly $C_1$–$C_3$-alkyl groups.

Suitable polymers with quaternary amino groups are, for example, the polymers described in the CTFA[2] Cosmetic Ingredient Dictionary under the name polyquaternium, such as methylvinylimidazolium chloride/vinyl pyrrolidone copolymer (polyquaternium 16), quaternized vinylpyrrolidone/dimethylaminoethyl methacrylate copolymer (polyquaternium 11), homopolymers and copolymers of dimethyldiallylammonium chloride (polyquaternium 6 and 7), quaternized hydroxyethylcellulose (polyquaternium 10) or quaternized guar derivatives.

[2] CTFA=Cosmetics, Toiletry and Fragrance Association—Translator

Suitable among the cationic polymers that can be contained in the composition of the invention is, for example, polyvinylpyrrolidone/dimethylaminoethyl methacrylate copolymer. Other cationic polymers are, for example, the copolymer of polyvinylpyrrolidone and imidazolimine methochloride, the terpolymer of dimethyldiallylammonium chloride, sodium acrylate and acrylamide, the terpolymer of vinylpyrrolidone, dimethylaminoethyl methacrylate and vinylcaprolactam, quaternized ammonium salts of hydroxyethylcellulose and a trimethylammonium-substituted epoxide and vinylpyrrolidone/methacrylamidopropyltrimethylammonium chloride copolymers.

Other suitable hair-strengthening polymers are the copolymers of vinylpyrrolidone, vinylcaprolactam and a dialkylaminoalkylmethacrylamide wherein the alkyl groups preferably contain 1 to 3 carbon atoms. Particularly preferred are the terpolymers of vinylpyrrolidone, vinylcaprolactam and dimethylaminopropylmethacrylamide. (DMAPMA) sold by ISP under the tradename Aquaflex® SF-40.

The hair-strengthening polymers preferred for the compact hair sprays of the invention are selected from among the copolymers of acrylates and acrylate hydroxyesters, copolymers of methyl vinyl ether and an alkyl monoester of maleic acid, copolymers of acrylic acid or methacrylic acid and an alkyl acrylate or alkyl methacrylate, copolymers of vinyl acetate and crotonic acid, copolymers of vinyl acetate and crotonic acid, copolymers of vinyl acetate, crotonic acid and vinyl alkanoates, copolymers of acrylic acid or methacrylic acid and an alkyl acrylate or alkyl methacrylate and an acrylamide or methacrylamide, polyvinylcaprolactam, vinylpyrrolidone/vinyl acetate copolymers, copolymers of vinylpyrrolidone, vinylcaprolactam and dialkylaminoalkylacrylamides or dialkylaminoalkylmethacrylamides, shellac, copolymers of alkylacrylamides, alkylaminoalkyl methacrylates and two or more monomers consisting of acrylic acid, methacrylic acid or an ester thereof and acrylate/acrylamide copolymers and mixtures of said polymers. Particularly preferred among these are the hair-strengthening polymers selected from among acrylate/acrylamide copolymers, the copolymers of alkylacrylamides, alkylaminoalkyl methacrylates and two or more monomers consisting of acrylic acid, methacrylic acid or an ester thereof, copolymers of vinyl acetate and crotonic acid, copolymers of vinyl acetate, crotonic acid and vinyl alkanoates, each in an amount of 8 to 30 wt. %, and polyvinylpyrrolidone/vinyl acetate copolymers in an amount of more than 10 to 30 wt. %.

The hair-strengthening polymer is preferably used in an amount greater than 4 wt. %, more preferably greater than 8 to 30 wt. % and particularly greater than 10 to 20 wt. %. The polymer is soluble or dispersible in the solvent mixture of the invention.

Suitable alcoholic solvents are $C_1$–$C_4$-alcohols, namely methanol, ethanol, isopropanol, n-propanol and butanol, of which ethanol and isopropanol are particularly preferred. The alcoholic solvent is preferably used in an amount from 20 to 80 wt. %, more preferably from 40 to 75 wt. % and particularly from 50 to 70 wt. %.

An essential component of the compact hair spray product of the invention is an organic solvent additive which is liquid under normal conditions (20° C., 1013 mbar) and which reduces the viscosity of the hair spray concentrate while at the same time increasing the vapor pressure of said concentrate. This solvent additive is preferably used in an amount from 1 to 50 wt. %, more preferably from 4 to 40 wt. % and particularly from 8 to 30 wt. %. Suitable additives are, in particular, the linear, branched or cyclic $C_5$ or $C_6$ alkanes or mixtures thereof, namely n-pentane, isopentane, neopentane, n-hexane, or the branched hexane isomers. Particularly preferred are the pentanes, particularly n-pentane. These additives reduce the viscosity of the concentrated polymer composition. A markedly higher-than-usual concentration is required to make a compact design possible. Because of the reduced viscosity of the hair spray concentrate, the resistance to flow is reduced when the spray pump is actuated so that more energy is available for atomizing the concentrate, which presumably is the reason for a finer spray and a reduced droplet size. As a result of the reduced vapor pressure of the overall composition, part of the solvent vaporizes spontaneously at the exit from the spray nozzle, which leads to a further reduction in droplet size and better nebulization of the spray. The vapor pressure of the organic solvent additive must thus be higher than that of the solvent used, but low enough to ensure that under normal conditions the additive is in liquid form. When substances that are gaseous at room temperature are used, a compact design is not feasible because of the gas space required. Moreover, under normal conditions, gaseous substances such as the common propellants propane and butane have the drawback that they vaporize immediately upon exiting the nozzle so that essentially only the concentrate reaches the hair, said concentrate not flowing adequately on the hair because of its viscosity.

Another preferred component of the compact hair spray product of the invention is a solvent additive capable of retarding drying (a4). Without this additive, the sprayed-on composition dries too fast on the treated hair, the sprayed-on composition does not flow sufficiently on the hair and as a result the phenomenon known as the pearl chain effect takes place. This means that only pointwise polymer depositions are observed on the hair, and there is no sufficient film formation and cross-linking of the hair. Water is the preferred drying-retarding additive. Other liquid, drying time-extending substances are also conceivable, for example polyhydric alcohols, such as, for example, glycols, such as ethylene glycol and propylene glycols, or glycerol or even longer-chain alcohols. The drying-retarding solvent additive is preferably used in an amount from 1 to 20 wt. %, more preferably from 2 to 16 wt. % and particularly from 4 to 12 wt. %.

The hair spray concentrate according to the invention can contain additional, common cosmetic additives, for example plasticizers such as glycerol, glycol, phthalate esters or citrate esters, perfumes, perfume oils, light-protective agents, UV filters, hair-care additives, combability improvers, moisturizers, dyes, corrosion inhibitors, antioxidants and preservatives, each in an amount from 0.01 to 10 wt. %, the total amount of additives ranging from 0.01 to 20 wt. %.

The container of the compact hair spray product of the invention can be made of any material as long as the material is sufficiently resistant to the slightly elevated internal pressure, brought about by the vapor pressure-raising organic solvent additive, and sufficiently diffusion-proof for the organic solvent additive. Suitable materials are, for example, the metals usually employed for aerosol packages, such as aluminum or tinplate. Preferred, however, are transparent or at least translucent materials allowing the product consistency and/or amount of composition in the container to be seen from the outside. The product container is preferably made essentially of polyethylene terephthalate (PET)

The spray pump used for the compact hair spray product of the invention has a maximum lift of 0.12 mL, preferably from 0.075 to 0.115 mL and particularly from 0.08 to 0.11 mL. Moreover, the spray pump is of the pilot pressure buildup design, meaning that when the pump is actuated, the pressure is allowed to build up before the spray is released. This results in a finer spray and further reduction in droplet size.

The composition of the hair spray concentrate places special requirements on the material of which the spray pump is made. The cylinder of a common spray pump for pump hair sprays is made of a plastic such as, for example, polypropylene, which can swell in contact with the organic solvent additives, for example pentane. Such a standard pump fails after some time. According to the invention, a spray pump is used which in the cylinder region is made of a material that essentially resists swelling by the organic solvent additive. Such a material is, for example, polyoxymethylene (POM). A spray pump suitable according to the invention is, for example, the Seaquist-Perfect PZ1/100 HVT fine-spray pump.

In contrast to the common spray pumps, a venting orifice is not needed, because the gas space formed upon emptying is filled by the highly volatile, evaporating organic solvent additive, and no air needs to be introduced. Even though the presence of a venting orifice is acceptable because the slight loss of organic solvent additive, a pump without a venting orifice is preferred.

The compact hair spray product of the invention is characterized in that it permits the production of hair spray products of compact design, that compared to conventional pump sprays it generates a less pronounced wetness effect and dries in a shorter time, and that in terms of application properties it approximates the conventional hair sprays. It can thus be viewed as a novel product type between a conventional pump hair spray and a conventional aerosol hair spray.

A few essential properties of a typical compact hair spray product of the invention are presented in the following table in comparison with the properties of a common pump hair spray and a common aerosol hair spray.

|  | Compact Hair Spray | Pump Hair Spray | Aerosol Hair Spray |
| --- | --- | --- | --- |
| Polymer content, wt. % | 10–20 | 3–8 | 2–6 |
| Packing volume, mL | 60 | 150 | 250 |
| Amount applied, g | 1.5 | 3.5 | 5.0 |
| No. of applications/100 mL | 52 | 24 | 14 |
| Economy of use | 4-fold | 2-fold | 1-fold |
| Applications/package | 31 | 36 | 35 |
| dv(50), μm | about 78 | about 80 | about 39 |
| Drying time | good | poor | good |

Compared to the common pump spray, the compact spray of the invention has about twice the economy of use and shows substantially better drying approximating that obtained with an aerosol hair spray. Compared to a common aerosol spray, the economy of use is even four times higher.

The following examples will illustrate the object of the invention in greater detail.

EXAMPLES

Example 1

Hair Spray Concentrate:

| | |
|---|---|
| 20.0 g | of pentane |
| 12.0 g | of acrylates/acrylamide copolymer (Ultrahold ® 8, BASF) |
| 5.0 g | of water |
| 1.16 g | of aminomethylpropanol |
| 0.45 g | of perfume |
| 0.36 g | of dimethicone copolyol |
| 0.36 g | of triethyl citrate |
| to 100 g | ethanol |

The hair spray concentrate was charged to a tubular 40-mL container made of translucent polyethylene terephthalate. The charged container was provided with a fine-spray pump, model Seaquist-Perfect PZ1/100 HVT, with a pump lift of 0.1 mL.

Example 2

Hair Spray Concentrate:

| | |
|---|---|
| 20.0 g | of pentane |
| 15.0 g | of acrylates/acrylamide copolymer (Ultrahold ® 8, BASF) |
| 5.0 g | of water |
| 1.45 g | of aminomethylpropanol |
| 0.45 g | of perfume |
| 0.45 g | of dimethicone copolyol |
| 0.45 g | of triethyl citrate |
| to 100 g | ethanol |

The hair spray concentrate was charged to a tubular 60-mL container made of translucent polyethylene terephthalate. The charged container was provided with a fine-spray pump, model Seaquist-Perfect PZ1/100 HVT, with a pump lift of 0.1 mL. The number of applications was close to that from a 250-mL aerosol spray can. The following values were determined for the droplet size distribution: dv(50)=78 µm, dv(90)=109 µm.

Example 3

Hair Spray Concentrate:

| | |
|---|---|
| 20.0 g | of pentane |
| 12.0 g | of vinyl acetate/crotonic acid/vinyl neodecanoate terpolymer (Resyn 28-2930, National Starch) |
| 5.0 g | of water |
| 1.24 g | of aminomethylpropanol |
| 0.45 g | of perfume |
| 0.72 g | of dimethicone copolyol |
| to 100 g | ethanol |

The hair spray concentrate was charged to a tubular 40-mL container made of translucent polyethylene terephthalate. The charged container was provided with a fine-spray pump, model Seaquist-Perfect PZ1/100 HVT, with a pump lift of 0.1 mL.

Example 4

Hair Spray Concentrate:

| | |
|---|---|
| 20.0 g | of pentane |
| 15.0 g | of VA/crotonates copolymer (Resyn 28-1310, National Starch) |
| 5.0 g | of water |
| 1.55 g | of aminomethylpropanol |
| 0.45 g | of perfume |
| 0.90 g | of triethyl citrate |
| to 100 g | ethanol |

The hair spray concentrate was charged to a tubular 60-mL container made of translucent polyethylene terephthalate. The charged container was provided with a fine-spray pump, model Seaquist-Perfect PZ1/100 HVT, with a pump lift of 0.1 mL. The number of applications was close to that from a 250-mL aerosol spray can.

What is claimed is:

1. A compact hair spray product comprising
a hair spray concentrate having a viscosity permitting good sprayability;
a pressure-tight and diffusion-proof container containing said hair spray concentrate; and
a fine-spray pump associated with the pressure-tight and diffusion-proof container for spraying said hair spray concentrate;
wherein said hair spray concentrate contains at least one hair-strengthening polymer; an alcoholic solvent for said at least one hair-strengthening polymer and at least one organic solvent additive;
wherein said at least one organic solvent additive is liquid under normal conditions, is capable of reducing viscosity of said concentrate and is capable of increasing vapor pressure of said concentrate; and
wherein said fine-spray pump has a cylindrical region made of a swelling-resistant material, said swelling-resistant material resists swelling by said at least one organic solvent additive, said fine-spray pump has a maximum lift of 0.12 mL and said fine-spray pump has pilot pressure buildup.

2. The compact hair spray product as defined in claim 1, containing greater than 10 percent by weight, based on said concentrate, of said at least one hair-strengthening polymer.

3. The compact hair spray product as defined in claim 1, wherein said at least one hair-strengthening polymer is selected from the group consisting of copolymers of acrylates and acrylate hydroxyesters; copolymers of methyl vinyl ether and an alkyl monoester of maleic acid; copolymers of acrylic or methacrylic acid and alkyl acrylate or alkyl methacrylate esters; vinyl acetate/crotonic acid copolymer; copolymers of vinyl acetate, crotonic acid and vinyl alkanoates; copolymers of acrylic or methacrylic acid, alkyl acrylate or alkyl methacrylate esters and acrylamides or methacrylamides; polyvinylcaprolactam; vinylpyrrolidone/vinyl acetate copolymer; copolymers of vinylpyrrolidone, vinylcaprolactam and dialkyl aminoalkylacrylamides or dialkylaminoalkylmethacrylamides; shellac; copolymers of alkylacrylamides, alkylaminoalkyl methacrylates and two or more monomers, said monomers each consisting of acrylic acid, methacrylic acid or an ester thereof; and acrylate/acrylamide copolymer; and wherein alkyl groups of said copolymers each contain from one to seven carbon atoms.

4. The compact hair spray product as defined in claim 3, containing from more than 10 percent by weight to 30 percent by weight, based on said concentrate, of said at least one hair-strengthening polymer, and wherein said at least one hair-strengthening polymer comprises said vinylpyrrolidone/vinyl acetate copolymer.

5. The compact hair spray product as defined in claim 1, containing from 8 to 30 percent by weight, based on said concentrate, of said at least one hair-strengthening polymer, and wherein said at least one hair-strengthening polymer is selected from the group consisting of acrylate/acrylamide copolymers; copolymers of alkylacrylamides, alkylaminoalkyl methacrylates and two or more monomers, said monomers each consisting of acrylic acid, methacrylic acid or an ester thereof; copolymers of vinyl acetate and crotonic acid and copolymers of vinyl acetate, crotonic acid and vinyl alkanoates; and wherein alkyl groups of said copolymers each contain from one to seven carbon atoms.

6. The compact hair spray product as defined in claim 1, wherein said alcoholic solvent comprises at least one monohydric $C_1$–$C_4$-alcohol.

7. The compact hair spray product as defined in claim 1, wherein said at least one organic solvent additive comprises at least one linear, branched or cyclic $C_5$–$C_6$ hydrocarbon.

8. The compact hair spray product as defined in claim 7, wherein said at least one linear, branched or cyclic $C_5$–$C_6$ hydrocarbon is selected from the group consisting of n-pentane, isopentane and neopentane.

9. The compact hair spray product as defined in claim 1, further comprising a drying-retarding solvent additive.

10. The compact hair spray product as defined in claim 9, wherein the drying-retarding solvent additive is water.

11. The compact hair spray product as defined in claim 1, wherein the pressure-tight and diffusion-proof container is made of a transparent or translucent material, so that the concentrate in the container is visible to an outside observer.

12. The compact hair spray product as defined in claim 1, wherein the pressure-tight and diffusion-proof container is made of polyethylene terephthalate.

13. The compact hair spray product as defined in claim 1, wherein the cylindrical region of the fine-spray pump is made of swelling-resistant polyoxymethylene material.

14. The compact hair spray product as defined in claim 1, wherein the lift of the fine-spray pump is from 0.08 to 0.11 mL.

* * * * *